US00PP35268P2

(12) United States Plant Patent
van Aart

(10) Patent No.: US PP35,268 P2
(45) Date of Patent: Jul. 18, 2023

(54) ***CORNUS* PLANT NAMED 'CORHEESFT'**

(50) Latin Name: *Cornus kousa*
Varietal Denomination: CORHEESFT

(71) Applicant: Van Heesbeen Cultures B.V., Rijsbergen (NL)

(72) Inventor: Mario van Aart, Oudenbosch (NL)

(73) Assignee: Van Heesbeen Cultures B.V., Rijsbergen (NL)

( * ) Notice: Subject to any disclaimer, the term of this patent is extended or adjusted under 35 U.S.C. 154(b) by 0 days.

(21) Appl. No.: 17/803,882

(22) Filed: Jan. 9, 2023

(51) Int. Cl.
*A01H 5/00* (2018.01)
*A01H 6/00* (2018.01)

(52) U.S. Cl.
USPC ..... Plt./220

(58) Field of Classification Search
USPC ..... Plt./226, 216, 220
See application file for complete search history.

*Primary Examiner* — Karen M Redden
(74) *Attorney, Agent, or Firm* — Samuel R. McCoy, Jr.

(57) ABSTRACT

A new and distinct *Cornus kousa* plant named 'CORHEESFT' which is characterized by a broad spreading to broad-upright growth habit with a globular profile, uniquely variegated juvenile foliage, dark green and relatively large mature foliage, as well as the stability of these characteristics from generation to generation.

3 Drawing Sheets

Latin name of the genus and species: The Latin name of the genus and species of the novel variety disclosed herein is *Cornus kousa.*

Variety denomination: The inventive variety of *Cornus* disclosed herein has been given the variety denomination 'CORHEESFT'.

BACKGROUND OF THE INVENTION

Parentage: 'CORHEESFT' is a seedling selection which resulted from the controlled pollination of an unnamed *Cornus kousa* plant (not patented), the seed parent, with a second unnamed *Cornus kousa* plant (not patented), the pollen parent. Said cross was performed by the inventor at a commercial greenhouse in Aalters, Belgium in the year 2003. After approximately two years of evaluating the seedlings that resulted from said cross, one plant was discovered in 2005 which exhibited uniquely-colored juvenile foliage.

Asexual Reproduction: Asexual reproduction of the new cultivar 'CORHEESFT', by way of grafting, was first initiated in 2015 in Aalters, Belgium. Through four subsequent generations, the unique features of this cultivar have proven to be stable and true to type.

SUMMARY OF THE INVENTION

The cultivar 'CORHEESFT' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'CORHEESFT'. These characteristics in combination distinguish 'CORHEESFT' as a new and distinct *Cornus* cultivar:

1. *Cornus* 'CORHEESFT' exhibits a broad spreading to broad-upright growth habit with a globular profile; and 2. *Cornus* 'CORHEESFT' exhibits uniquely variegated juvenile foliage and dark green, relatively large mature foliage; and
3. *Cornus* 'CORHEESFT' exhibits juvenile foliage with a pale yellow-white adaxial surface that is heavily suffused with a mixture of orange-red and red near the base, lightly suffused with yellow-green elsewhere, and marbled, blotched, and margined with a mixture of white, green-white, and yellow-green; and
4. *Cornus* 'CORHEESFT' exhibits juvenile foliage with a white abaxial surface that is suffused with red near the base and marbled, blotched, and margined with a mixture of white, green-white and greyed-green.

BOTANICAL DESCRIPTION OF THE PLANT

Figure 1:
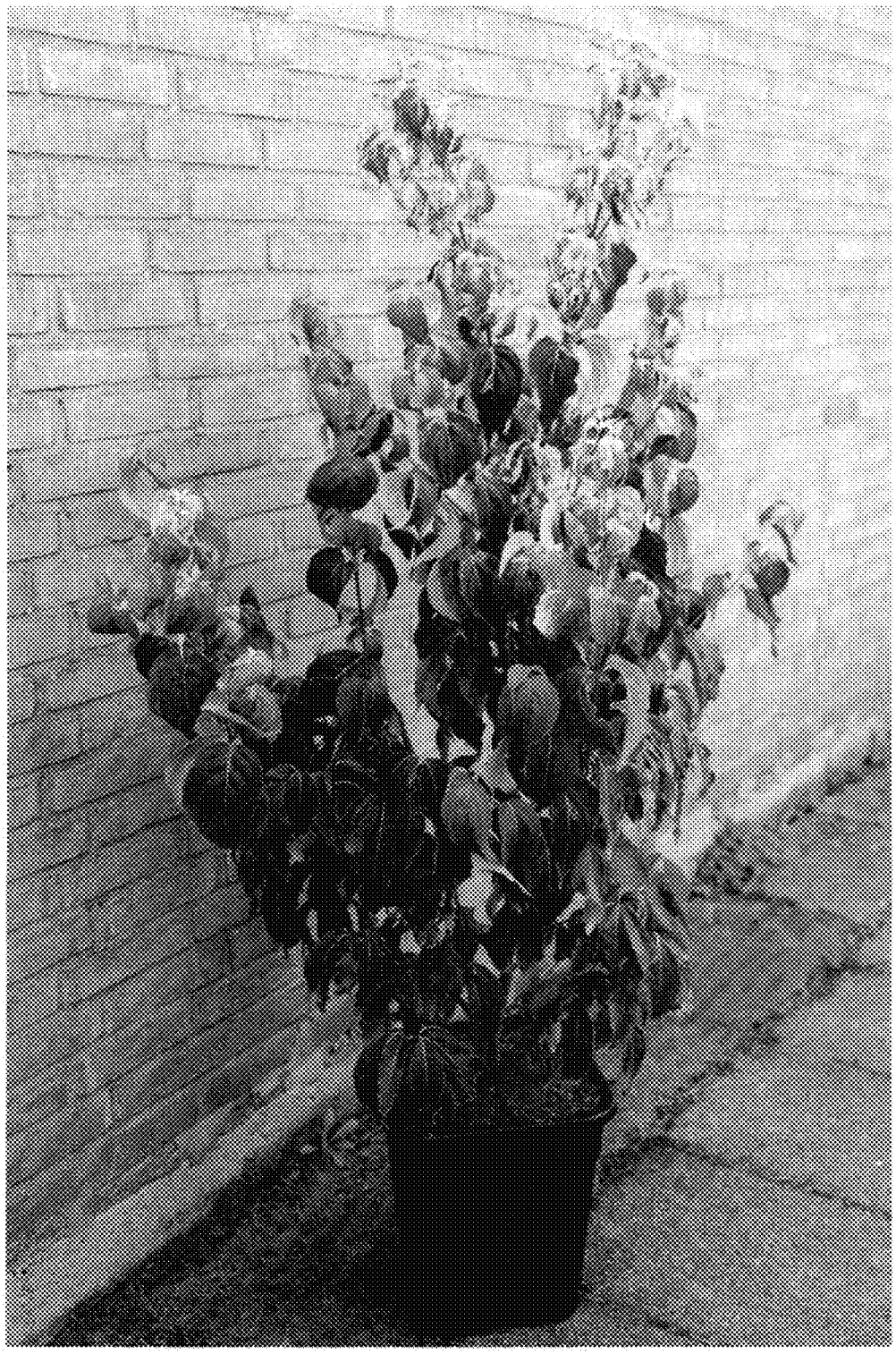
FIG. 1 illustrates, as nearly true as it is reasonably possible to make the same in color photographs of this type, an exemplary 12-month-old 'CORHEESFT' plant in a 13 cm nursery pot, grown in a greenhouse in Aalters, Belgium.
Figure 2:
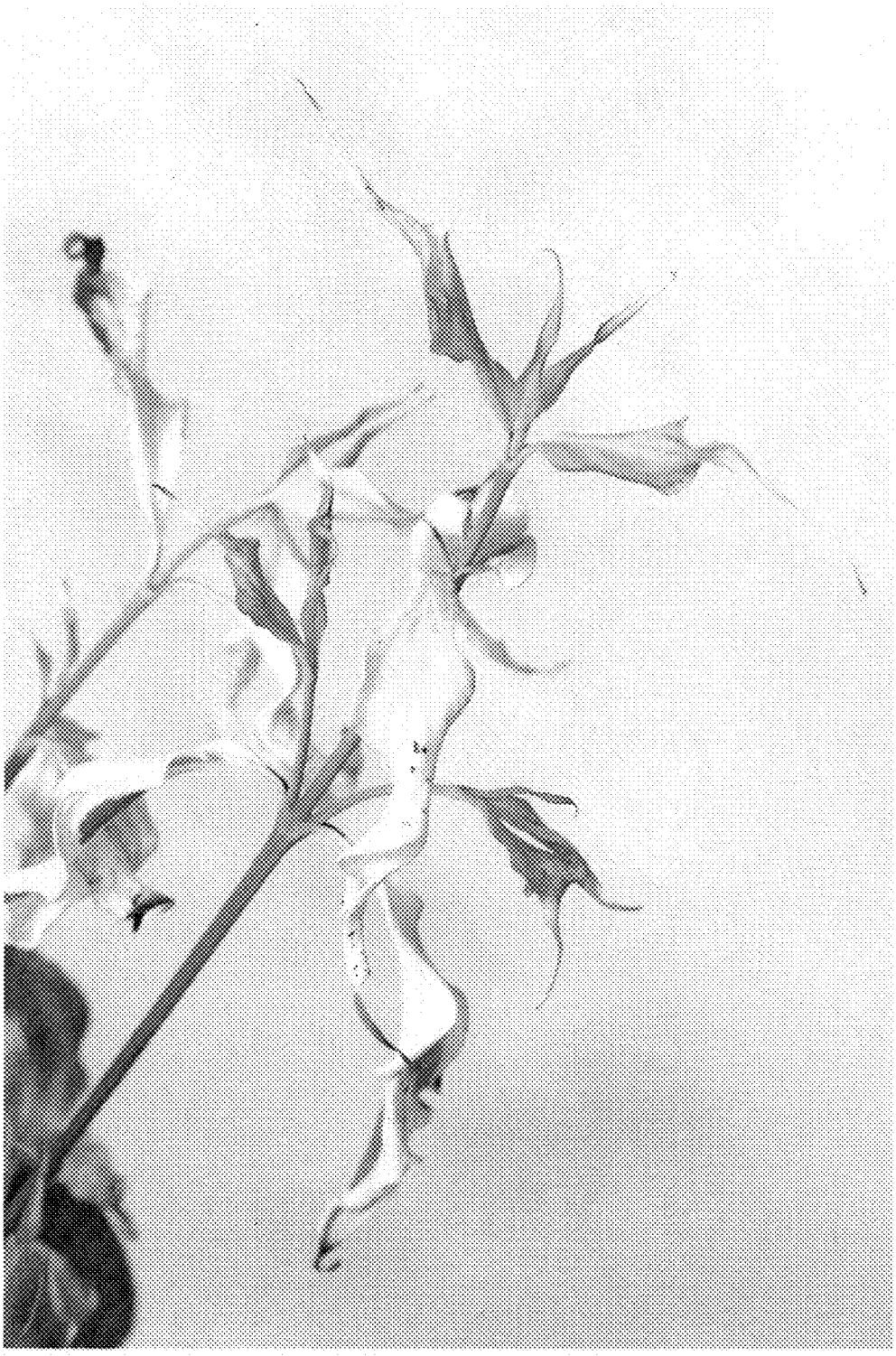
FIG. 2 illustrates, as nearly true as it is reasonably possible to make the same in color photographs of this type, the juvenile foliage of 'CORHEESFT'.
Figure 3:
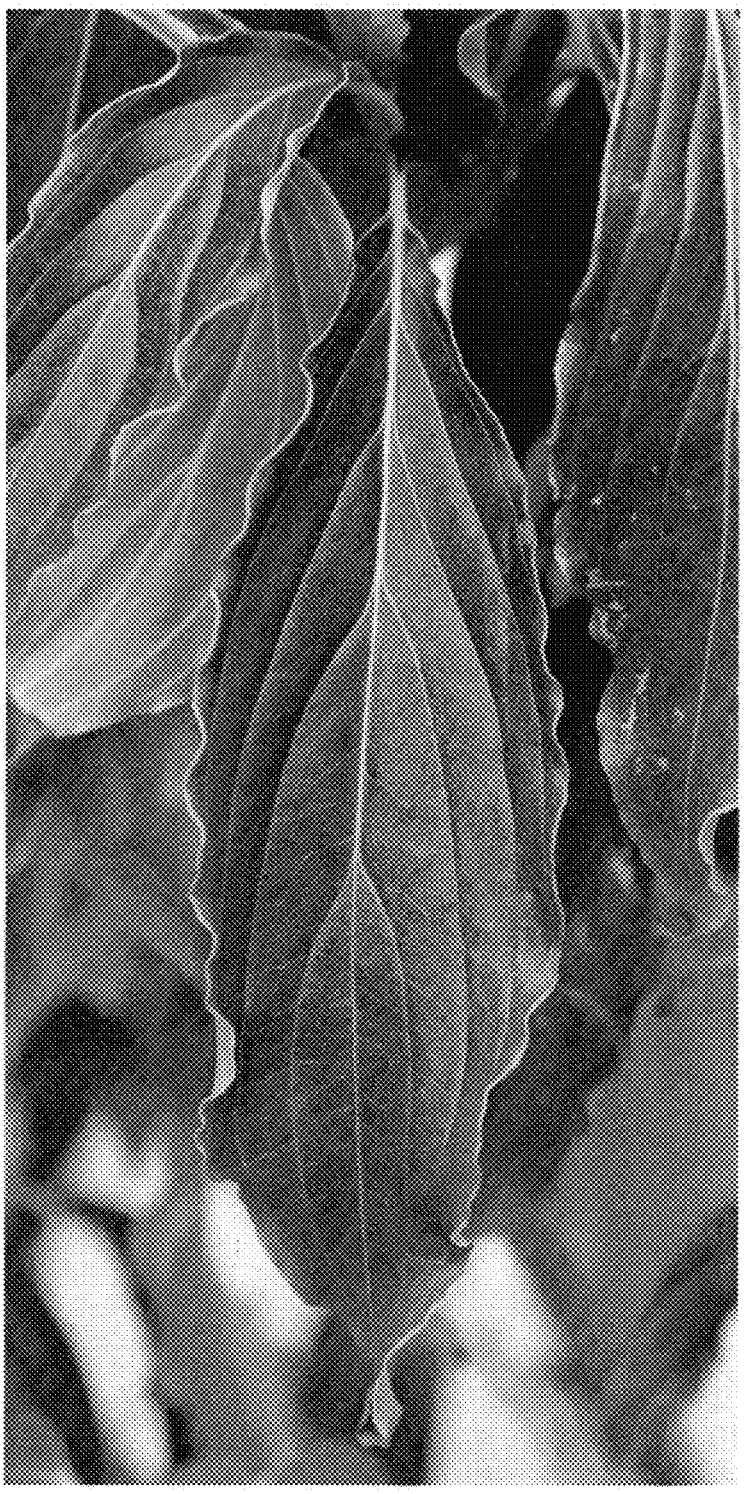
FIG. 3 illustrates, as nearly true as it is reasonably possible to make the same in color photographs of this type, the mature foliage of 'CORHEESFT'.

The following observations and measurements were made in August of 2022 and describes 24-month-old 'CORHEESFT' plants grown in a 24 cm nursery pot and produced in both an unheated greenhouse and grown outdoors in Aalters, Belgium. Plants were grown using conventional production protocols for *Cornus* which consisted of growing in full sun exposure with regular overhead irrigation and slow-release fertilizer applications as needed.

No pest or disease control measures were otherwise utilized in production. No photoperiodic treatments or artificial light was given to the plants.

Those skilled in the art will appreciate that certain characteristics will vary with older or, conversely, with younger plants. 'CORHEESFT' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'CORHEESFT' and comparisons with the parents and most similar commercial variety of *Cornus* are provided below.

Plant description:

*Growth habit*.—Deciduous shrub with a broad-upright to spreading-upright growth habit.

*Plant profile*.—Globular.

*Average height from base to top of foliage*.—132 cm.

*Average width*.—86.0 cm.

*Growth rate*.—Moderately fast growing.

*Plant vigor*.—Moderately vigorous.

*Propagation details*.—Asexual propagation is accomplished by grafting a scion onto rootstock.

*Time to produce a marketable plant*.—Approximately 2 years are required to produce a marketable 3-liter nursery container.

*Disease and pest resistance or susceptibility*.—Plants have not been observed to be susceptible or resistant to pathogens and pests common to *Cornus kousa*.

*Environmental tolerances*.—Adapt to at least USDA Zones 6 and 10; moderate tolerance to rain; moderate tolerance to wind; low tolerance to drought.

Root system:

*Density*.—Moderately dense.

*Distribution in the soil profile*.—Roots are relatively shallow.

*Texture*.—Fleshy; no root hairs present.

Stem:

*Branching habit*.—Basally branching main stem; freely branching with lateral branches.

*Number of main stems per plant*.—3.

*Number of lateral branches per plant*.—22.

*Aspect*.—Rounded.

*Length of main stems*.—61.0 cm.

*Diameter of main stems*.—0.8 cm at the widest point.

*Internode length on main stems*.—9.0 cm.

*Attitude*.—Upright; between 25 and 40 degrees from vertical.

*Strength*.—Strong.

*Texture*.—Glabrous; lenticels are present on mature stems, mature lateral branches, and oldest wood. Lenticels on the mature stems and branches predominantly occur at and near the axils and are linear in shape; approximately 0.5 mm wide and varying in length. Lenticels on the oldest wood are orbicular, 0.5 mm in diameter.

*Luster*.—Matte.

*Color, juvenile*.—Red, nearest to RHS 48C; progressively suffused with a combination of a darker shade of red and greyed-red, nearest to RHS 53B, 52B, and 182A, as stems mature.

*Color, mature*.—Nearest to a mixture of greyed-orange and grey-brown, RHS 177B and N199C; lenticels are colored greyed-brown, nearest to a combination of RHS 199B and 199C.

*Color, internodes*.—Nearest to a mixture of greyed-orange and grey-brown, RHS 177B and N199C; lenticels are colored greyed-brown, nearest to a combination of RHS 199B and 199C.

*Color, oldest wood*.—Greyed-brown, nearest to RHS 199A; densely covered with orbicular lenticels which are colored greyed-brown, nearest to RHS 199A.

Foliage:

*Arrangement*.—Opposite.

*Division*.—Simple.

*Attachment*.—Petiolate.

*Quantity*.—Average of 14 leaves per lateral branch.

*Lamina*.—Dimensions — 14.7 cm long and 7.6 cm wide, on average. Shape — Ovate to near elliptic. Aspect — Slightly carinate and moderately curled downward; apex is slightly spiraled and curled. Apex — Apiculate. Base — Obtuse to long attenuate. Margin — Entire; moderately to strong undulated. Pubescence, texture and luster of adaxial surface — Pubescent, smooth, and slightly to moderately glossy; sparsely covered with very short, adpress hairs with an average length of 0.2 mm and colored white, nearest to RHS RHS 155D. Pubescence, texture and luster of abaxial surface — Pubescent, smooth, and matte; sparsely covered with very short, adpress hairs with an average length of 0.2 mm and colored white, nearest to RHS 155D. Color — Juvenile foliage, adaxial surface — Proximal one-third portion of the laminar surface is yellow-white, nearest to RHS 158D, and heavily suffused with a mixture of orange-red and red, RHS 35B and 37A; distal two-thirds portion of the laminar surface is yellow-white, nearest to RHS 158D, and suffused with yellow-green, nearest to a mixture of RHS 144A and 144B; sparsely to moderately blotched, marbled and margined with a combination of white, green-white and yellow-green, nearest to RHS 155C, 157A, and 147D; veined yellow-green, nearest to RHS 145B. As foliage matures, it becomes progressively suffused with yellow-green, RHS 147A. Juvenile foliage, abaxial surface — White, nearest to RHS 155C, with the proximal one-third portion of the laminar surface suffused with red, nearest to RHS 39D; sparsely blotched, marbled and margined with a combination of white, green-white and greyed-green, nearest to RHS 155C, N155A, and 189D. As foliage matures, it becomes progressively suffused with yellow-green, RHS N148D. Mature foliage, adaxial surface — Nearest to in between green and yellow-green, RHS 139A and 147A yet closest to 139A. Mature foliage, abaxial surface — Yellow-green, nearest to RHS N148B. Venation — Pattern — Arcuate and cross-venulate. Venation color, adaxial surface — Yellow-green, nearest to RHS N144C; occasionally suffused with greyed-red towards the base, nearest to a mixture of RHS 179A, 179B, and 179C. Venation color, abaxial surface — Yellow-green, nearest to RHS 150D; becoming darker towards the base, nearest to RHS 151C.

*Petiole*.—Length —1.15 cm. Width — 0.25 cm. Texture — Smooth and glabrous. Luster — Matte. Strength — Strong. Color, adaxial surface — Yellow-green, nearest to RHS 154C; occasionally suffused with greyed-red, nearest to a mixture of RHS 179B and 179C; base of the petiole is brown, nearest to RHS 200A yet darker. Color, abaxial surface — Yellow-green, nearest to a combination of RHS 146D, 151B, and 151C.

Inflorescence: Not yet observed.

Bud: Not yet observed.

Flower: Not yet observed.

Reproductive organs: Not yet observed.

Seed and fruit: Not yet observed.

COMPARISONS WITH THE PARENT PLANTS

Plants of the new cultivar 'CORHEESFT' differ from the seed parent, an unnamed and unpatented *Cornus kousa* plant, by the characteristics described in Table 1.

TABLE 1

| Characteristic | 'CORHEESFT' | The seed parent. |
|---|---|---|
| Plant size. | Smaller than the seed parent. | Larger than 'CORHEESFT'. |
| Foliage size. | Larger than the seed parent. | Smaller than 'CORHEESFT'. |
| General coloration of the juvenile foliage. | Pale yellow-white; heavily suffused with a mixture of orange-red and red near the base, and lightly suffused with yellow-green elsewhere; marbled, blotched, and margined with a mixture of white, green-white, and yellow-green. | Yellow-green, and suffused with a mixture of orange-red and red near the base. |
| General coloration of the juvenile foliage; abaxial surface. | White, suffused with red near the base and marbled, blotched, and margined with a mixture of white, green-white and greyed-green. | Yellow-green and suffused with a mixture of orange-red and red near the base. |

Plants of the new cultivar 'CORHEESFT' differ from the pollen parent, an unnamed and unpatented *Cornus kousa* plant, by the characteristics described in Table 2.

TABLE 2

| Characteristic | 'CORHEESFT' | The pollen parent. |
|---|---|---|
| Growth habit. | Broad-upright to spreading-upright. | Upright. |
| Foliage size. | Larger than the pollen parent. | Smaller than 'CORHEESFT'. |
| General coloration of the juvenile foliage. | Pale yellow-white; heavily suffused with a mixture of orange-red and red near the base, and lightly suffused with yellow-green elsewhere; marbled, blotched, and margined with a mixture of white, green-white, and yellow-green. | Yellow-green and suffused with a mixture of orange-red and red near the base. |
| General coloration of the juvenile foliage; abaxial surface. | White, suffused with red near the base and marbled, blotched, and margined with a mixture of white, green-white and greyed-green. | Yellow-green and suffused with a mixture of orange-red and red near the base. |

COMPARISON WITH THE MOST SIMILAR *CORNUS* CULTIVAR KNOWN TO THE INVENTOR

Plants of the new cultivar 'CORHEESFT' differ from the commercial variety, *Cornus* 'Pink Lips' (not patented), in the following characteristics described in Table 2 below.

TABLE 2

| Characteristic | 'CORHEESFT' | 'Pink Lips' |
|---|---|---|
| Bloom period. | Spring. | Summer. |
| Foliage size. | Larger than 'Pink Lips'. | Smaller than 'CORHEESFT'. |
| General coloration of the juvenile foliage; adaxial surface. | Pale yellow-white; heavily suffused with a mixture of orange-red and red near the base, and lightly suffused with yellow-green elsewhere; marbled, blotched, and margined with a mixture of white, green-white, and yellow-green. | Mottled with pale yellow-white and yellow-green, and heavily suffused with red-purple. |

That which is claimed is:

1. A new and distinct *Cornus kousa* plant named 'CORHEESFT', substantially as described and illustrated herein.

* * * * *